(12) United States Patent
Vandana et al.

(10) Patent No.: US 6,638,544 B2
(45) Date of Patent: Oct. 28, 2003

(54) PROCESS FOR THE PREPARATION OF HYDROXYLATED LECITHIN FROM CRUDE SOYBEAN LECITHIN

(75) Inventors: Vemulapalli Vandana, Hyderabad (IN); Marellapudi Sri Lakshmi Karuna, Hyderabad (IN); Potharaju Seetharamanjaneya Sai Prasad, Hyderabad (IN); Rachapudi Badari Narayana Prasad, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/105,965

(22) Filed: Mar. 25, 2002

(65) Prior Publication Data

US 2003/0180403 A1 Sep. 25, 2003

(51) Int. Cl.$^7$ ................................................ A61K 35/78

(52) U.S. Cl. ........................................ 424/757; 424/725
(58) Field of Search .................................. 424/757, 725

(56) References Cited

FOREIGN PATENT DOCUMENTS

JP          1-151525 A    *  6/1989

* cited by examiner

Primary Examiner—Leon B. Lankford, Jr.
Assistant Examiner—Susan D Coe
(74) Attorney, Agent, or Firm—Ladas & Parry

(57) ABSTRACT

The invention relates to a microwave assisted process for the preparation of hydroxylated lecithin from soybean lecithin comprising hydroxylating crude soybean lecithin by using hydrogen peroxide and lactic acid as hydroxylating agent through microwave irradiation.

5 Claims, No Drawings

PROCESS FOR THE PREPARATION OF HYDROXYLATED LECITHIN FROM CRUDE SOYBEAN LECITHIN

The present invention relates to a process for the preparation of hydroxylated lecithin from crude soybean lecithin.

The invention particularly relates to a simple and rapid microwave-assisted process for the preparation of hydroxylated lecithin from soybean lecithin. The commercial soybean lecithin is hydroxylated very rapidly using hydrogen peroxide and lactic acid in microwave irradiation conditions compared to traditional thermal reaction conditions. Microwave heating has the unique feature of providing environmentally friendly processes.

BACKGROUND OF THE INVENTION

Commercial soybean lecithin is an important co-product of oil processing obtained during degumming step of oil refining. Soybean lecithin is a complex mixture and comprises phospholipids, triglycerides, with minor amounts of other constituents like phytoglycolipids, phytosterols, tocopherols and fatty acids. The major phospholipids present in vegetable lecithins are phosphatidylcholine, phosphatidylethanolamine and phosphatidylinositol. Soybean lecithin has potential as a multifunctional additive for food, pharmaceutical and industrial applications. The primary usage of Soybean lecithin in food is as an emulsifier. (Dashiell, G. L., in Lecithins: Sources, Manufacture and Uses (AOCS Monograph), edited by B. F. Szuhaj, American Oil Chemical Society, Champaign III, 1989, p. 213). An effective way to improve water dispersability or enhance emulsifying properties of vegetable lecithins for o/w system is hydroxylation. The pronounced "hydrophilic" character enables the products to be dispersed easily in cold water. Hydrogen peroxide reacts with the double bonds of unsaturated phospholipid fatty acids under the catalytic action of organic acids of low molecular weight (e.g., lactic acid) to form dihydroxy fatty acid derivatives. Hydroxylation imparts hydrophilic properties and improves moisture retention to the lecithin. Hydroxylated lecithin is a light colored product with increased water dispersability. It is useful in baking applications where it can improve the dispersion of fats and retard staling (Schmidt, J. C, and Orthoefer, in Lecithins, edited by B. F. Szuhaj and G. R. List, American Oil Chemical Society, Champaign III, 1985, pp. 203–211).

Hydroxylation involves insertion of hydroxyl groups at the points of unsaturation in phospholipid fatty acid [U.S. Pat. No. 2,629,662 (1953)]. This process involves blending of 14% of 100-volume hydrogen peroxide in the presence of an organic acid such as lactic acid or peracetic acid or tartaric acid or citric acid at elevated temperatures (40 to 75° C.) for about 10% reduction in Iodine Value in about 1 to 3 hours of reaction time. The inventors used very high concentration of hydrogen peroxide for the hydroxylation reaction and the phospholipids may get degraded due to the exposure of the lecithin to higher temperatures for longer reaction periods.

The objective of the present invention is to provide an improved process for the hydroxylation of crude soybean lecithin using lower concentrations of hydrogen peroxide solution with higher conversion rates at lower reaction times. The Iodine Value reduction of the crude soybean lecithin through microwave-assisted reaction in 40 minutes is about 37%, which could not be achieved using the conventional heating even after 18 hr in similar reaction conditions. Similarly less than 5 minutes time is sufficient to achieve 10% reduction in IV of hydroxylated lecithin.

OBJECTS OF THE INVENTION

The main objective of the present invention is to provide an improved process for the hydroxylation of crude soybean lecithin.

Another objective of the present invention is to develop a simple environmentally friendly method wherein microwave irradiation technique is used instead of traditional thermal heating.

Yet another objective of the present invention is to use lower concentration of hydrogen peroxide (30%) as the high concentrations tend to cause decomposition of lecithin.

Yet another object of the present invention is to bring down the hydroxylation time drastically with enhanced hydroxylation using microwave irradiation technique without exposing the lecithin to longer hours of reaction.

SUMMARY OF THE INVENTION

Accordingly the present invention provides an improved process for the preparation of hydroxylated lecithin from soybean lecithin, which comprises hydroxylating crude soybean lecithin by using about 30% hydrogen peroxide in the range of 1–4 w % of lecithin and about 75% lactic acid in the range 12–18 w % of lecithin, as hydroxylating agent through microwave irradiation, at a temperature ranging between 50 to 70° C., at microwave power of 300 to 600 W for a period of 5–60 min to obtain the desired product. In an embodiment of the present invention the starting material used is crude soybean lecithin. In an another embodiment the amount of hydrogen peroxide used in the reaction mixture is preferably 3% of lecithin. In yet another embodiment the amount of lactic acid peroxide used in the reaction mixture is preferably 15% of lecithin. In yet another embodiment the reaction is carried out preferably at 300 to 600 W microwave power. In yet another embodiment the reaction is carried out preferably for a period in the range of 5–40 min. In still another embodiment the reduction of iodine value in hydroxylated lecithin is about 20 to 37%.

The following examples are given by way of illustration and therefore should not be construed to limit the scope of the present invention.

EXAMPLE 1

Soybean lecithin (10 g), having an iodine value of 99.5 was taken in a teflon tube and to this lactic acid (0.3 g, 3% of lecithin, wt/wt) and 30% hydrogen peroxide (1.5 ml, 15% of lecithin, vol/wt) were added and heated 70° C. in the microwave irradiation conditions using 600 W power in Microwave Lab Station for 5 minutes. The product was dried under reduced pressure till it becomes moisture free. The hydroxylated lecithin (10.25 g) was analyzed for iodine value and found to be 79.3.

EXAMPLE 2

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 10 minutes. The product was dried under reduced pressure till it becomes moisture free. The hydroxylated lecithin (10.24 g) was analyzed for iodine value and found to be 78.5.

EXAMPLE 3

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 15 minutes. The product was dried under reduced pressure till it becomes moisture free. The hydroxylated lecithin (10.25 g) was analyzed for iodine value and found to be 75.6

EXAMPLE 4

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 20 minutes. The product was dried under reduced pressure till it becomes moisture free. The hydroxylated lecithin (10.23 g) was analyzed for iodine value and found to be 72.4.

EXAMPLE 5

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 25 minutes. The product was dried under reduced pressure till it becomes moisture free. The hydroxylated lecithin (10.26 g) was analyzed for iodine value and found to be 69.4

EXAMPLE 6

Soybean lecithin (10 g), having an iodine value of 99.5 was taken in a teflon tube and to this 75% lactic acid (0.3 g, 3%. of lecithin, wt/wt) and 30% hydrogen peroxide (1.5 ml, 15% of lecithin, vol/wt) were added and heated to 70° C. in the microwave irradiation conditions using 600 W power in Microwave Lab Station for 35 minutes. The product was dried under reduced pressure till it becomes moisture free. The hydroxylated lecithin (10.25 g) was analyzed for iodine value and found to be 65.5.

EXAMPLE 7

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 40 minutes. The product was dried under reduced pressure till it becomes moisture free. The hydroxylated lecithin (10.24 g) was analyzed for iodine value and found to be 62.4.

EXAMPLE 8

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 600 W power in Microwave Lab Station for 60 minutes. The product was dried under reduced pressure till it becomes moisture free. The hydroxylated lecithin (10.25 g) was analyzed for iodine value and found to be 62.4.

EXAMPLE 9

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 400 W power in Microwave Lab Station for 5 minutes. The product was dried under reduced pressure till it becomes moisture free. The hydroxylated lecithin (10.23 g) was analyzed for iodine value and found to be 83.8.

EXAMPLE 10

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 400 W power in Microwave Lab Station for 10 minutes. The product was dried under reduced pressure till it becomes moisture free. The hydroxylated lecithin (10.24 g) was analyzed for iodine value and found to be 81.5.

EXAMPLE 11

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 500 W power in Microwave Lab Station for 5 minutes. The product was dried under reduced pressure till it becomes moisture free. The hydroxylated lecithin (10.24 g) was analyzed for iodine value and found to be 81.5.

EXAMPLE 12

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 70° C. in the microwave irradiation conditions using 500 W power in Microwave Lab Station for 5 minutes. The product was dried under reduced pressure till it becomes moisture free. The hydroxylated lecithin (10.24 g) was analyzed for iodine value and found to be 79.9.

EXAMPLE 13

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 50° C. in the microwave irradiation conditions using 600 W power in Microwave Lab Station for 10 minutes. The product was dried under reduced pressure till it becomes moisture free. The hydroxylated lecithin (10.25 g) was analyzed for iodine value and found to be 82.5.

EXAMPLE 14

Soybean lecithin (10 g), having an iodine value of 99.5 was taken in a teflon tube and to this 75% lactic acid (0.3 g, 3% of lecithin, wt/wt) and 30% hydrogen peroxide (1.5 ml, 15% of lecithin, vol/wt) were added and heated to 60° C. in the microwave irradiation conditions using 600 W power in Microwave Lab Station for 10 minutes. The product was dried under reduced pressure till it becomes moisture free. The hydroxylated lecithin (10.25 g) was analyzed for iodine value and found to be 80.9.

For comparison soybean lecithin was also hydroxylated using conventional thermal heating and the results are given as comparative examples.

COMPARATIVE EXAMPLE 1

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml, 15% of lecithin, vol/wt) were added and heated to the reactants to 70° C. with stirring. The contents were stirred for 2 hours and the product was dried under reduced pressure till it becomes moisture free. The hydroxylated lecithin (10.29 g) was analyzed for iodine value and found to be 82.5.

COMPARATIVE EXAMPLE 2

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml, 15% of lecithin, vol/wt) were added and heated to the reactants to 70° C. with stirring. The contents were stirred for 3 hours and the product was dried under reduced pressure till it becomes moisture free. The hydroxylated lecithin (10.26 g) was analyzed for iodine value and found to be 79.1.

COMPARATIVE EXAMPLE 3

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml, 15% of lecithin, vol/wt) were added and heated to the reactants to 70° C. with stirring. The contents were stirred for 5 hours and the product was dried under reduced pressure till it becomes moisture free. The hydroxylated lecithin (10.24 g) was analyzed for iodine value and found to be 76.1.

COMPARATIVE EXAMPLE 4

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml, 15% of lecithin, vol/wt) were added and heated to the reactants to 70° C. with stirring. The contents were stirred for 7 hours and the product was dried under reduced pressure till it becomes moisture free. The hydroxylated lecithin (10.26 g) was analyzed for iodine value and found to be 71.0%.

COMPARATIVE EXAMPLE 5

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml, 15% of lecithin, vol/wt) were added and heated to the reactants to 70° C. with stirring. The contents were stirred for 8 hours and the product was dried under reduced pressure till it becomes moisture free. The hydroxylated lecithin (10.27 g) was analyzed for iodine value and found to be 66.4.

COMPARATIVE EXAMPLE 6

Soybean lecithin (10 g), having an iodine value of 99.5 was taken in a round bottomed flask and to this 75% lactic acid (0.3 g, 3% of lecithin, wt/wt) and 30% hydrogen peroxide (1.5 ml 15% of lecithin, vol/wt) were added and heated the reactants to 70° C. with stirring. The contents were stirred for 18 hours and the product was dried under reduced pressure till it becomes moisture free. The hydroxylated lecithin (10.25 g) was analyzed for iodine value and found to be 64.8.

The main advantages of the present invention are:

1. The present invention is an improved process for the preparation of hydroxylated lecithin from crude soybean lecithin.
2. The present invention uses the traditional hydroxylating agents namely hydrogen peroxide solution and 75% 75% lactic acid
3. The present invention uses lower concentration of hydrogen peroxide (30%) as the high concentrations tend to cause decomposition of lecithin.
4. The present invention uses microwave irradiation technique instead of traditional thermal heating for rapid hydroxylation without exposing the lecithin to higher temperatures for longer reaction periods.
5. The present invention drastically reduces the hydroxylation time using microwave irradiation technique compared to conventional thermal heating. The comparative data on the hydroxylation of soybean lecithin using microwave-assisted and conventional heating are given in Table 1 and 2.

TABLE 1

Reduction in IV with respect to reaction time during hydroxylation of soybean lecithin at 70° C. and 600 W power using microwave-assisted process [Iodine Value (IV) of soybean lecithin: 99.5]

| Reaction time (min) | I.V. | % Reduction in IV |
|---|---|---|
| 5 | 79.3 | 20.3 |
| 10 | 78.5 | 21.1 |
| 15 | 75.6 | 24.0 |
| 20 | 72.4 | 27.2 |
| 25 | 69.4 | 30.3 |
| 35 | 65.5 | 34.2 |
| 40 | 62.4 | 37.3 |
| 60 | 62.4 | 37.3 |

TABLE 2

Reduction in IV with respect to reaction time during hydroxylation of soybean lecithin at 70° C. using conventional heating (Iodine Value of soybean lecithin: 99.5)

| Reaction time (Hrs) | I.V. | % Reduction in IV |
|---|---|---|
| 2 | 82.5 | 17.1 |
| 3 | 79.1 | 20.5 |
| 5 | 76.1 | 23.5 |
| 7 | 71.0 | 28.6 |
| 8 | 66.4 | 33.3 |
| 18 | 64.8 | 34.9 |

6. The present invention that is microwave-assisted reaction a higher percent of hydroxylation of soybean lecithin is achieved within 5 to 40 minutes compared to conventional heating methods without exposing the lecithin to longer hours of reaction. For example the reduction in IV in 5 minutes of microwave irradiation is more than that of 3 hours conventional heating conditions (Table 1 and 2).

We claim:

1. A process for preparation of hydroxylated lecithin from soybean lecithin, which comprises treating said soybean lecithin with from about 1 to 4% by weight of a 30% hydrogen peroxide solution based on the weight of lecithin and from about 12 to 18% by weight of a 75% lactic acid solution based on the weight of lecithin while subjecting the mixture of lecithin, hydrogen peroxide, and lactic acid to microwave irradiation at a power of from about 300 to 600 W at a temperature of from about 50 to 70° C. for a period of from about 5 to 60 minutes to obtain the desired product.

2. A process as claimed in claim 1, wherein the amount of hydrogen peroxide used in the reaction mixture is preferably 3% of lecithin.

3. A process as claimed in claim 1, wherein the amount of lactic acid peroxide used in the reaction mixture is preferably 15% of lecithin.

4. A process as claimed in claim 1, wherein the reaction is carried out for a period in the range of 5–40 min.

5. A process as claimed in claim 1 wherein the reduction of iodine value in hydroxylated lecithin is about 20 to 37%.

* * * * *